(12) United States Patent  
Webster (10) Patent No.: US 9,894,900 B2  
(45) Date of Patent: Feb. 20, 2018

(54) COMPACT FOR INSECT CONTROL

(76) Inventor: David Webster, Winchester (GB)

( * ) Notice: Subject to any disclaimer, the term of this patent is extended or adjusted under 35 U.S.C. 154(b) by 0 days.

(21) Appl. No.: 12/516,226

(22) PCT Filed: Nov. 23, 2007

(86) PCT No.: PCT/GB2007/004511  
§ 371 (c)(1),  
(2), (4) Date: May 26, 2009

(87) PCT Pub. No.: WO2008/062221  
PCT Pub. Date: May 29, 2008

(65) Prior Publication Data  
US 2010/0062944 A1 Mar. 11, 2010

(30) Foreign Application Priority Data  
Nov. 23, 2006 (GB) .................. 0623398.5

(51) Int. Cl.  
*A01N 25/08* (2006.01)  
*A01N 25/34* (2006.01)  
*C05F 11/00* (2006.01)  
*C05G 3/00* (2006.01)

(52) U.S. Cl.  
CPC ........... *A01N 25/34* (2013.01); *C05G 3/0041* (2013.01); *C05G 3/0047* (2013.01); *C05G 3/0052* (2013.01)

(58) Field of Classification Search  
None  
See application file for complete search history.

(56) References Cited

U.S. PATENT DOCUMENTS

| | | | |
|---|---|---|---|
| 2,821,500 A | 1/1958 | Jackson | |
| 3,132,067 A | 8/1960 | Rauscher | |
| 3,475,154 A | 10/1969 | Kato | |
| 4,170,630 A | 10/1979 | Young | |
| 6,001,346 A * | 12/1999 | Delwiche et al. | ............ 424/84 |
| 2009/0084024 A1 * | 4/2009 | Hamilton Baxter | ........... 43/131 |

FOREIGN PATENT DOCUMENTS

| | | | |
|---|---|---|---|
| EP | 0372796 A2 | 6/1990 | |
| EP | 0529975 A1 | 3/1993 | |
| FR | 2533415 A1 | 3/1984 | |
| JP | 55062001 | 5/1980 | |
| JP | 02288803 | 11/1990 | |
| WO | 95/14379 A1 | 6/1995 | |
| WO | 96/03041 A1 | 2/1996 | |
| WO | 97/33472 A1 | 9/1997 | |
| WO | 01/78509 A2 | 10/2001 | |
| WO | 03/051112 A1 | 6/2003 | |
| WO | WO03/051112 A1 * | 6/2003 | ............ A01N 25/00 |
| WO | 2004/062362 A2 | 7/2004 | |

* cited by examiner

*Primary Examiner* — Mina Haghighatian  
*Assistant Examiner* — Erin Hirt  
(74) *Attorney, Agent, or Firm* — William H. Holt (57) ABSTRACT

A compact comprising particles and an active agent selected from a pesticide, a herbicide, a plant nutrient, a fertilizer, an arthropod attractant such as a semiochemical, a semiochemical, a food or protein bait, and including mixtures of two or more thereof.

8 Claims, 5 Drawing Sheets

COMPACT FOR INSECT CONTROL

The present invention relates to arthropod control, and in particular insect control.

A number of ways of protecting plants, and in particular fruit and vegetable crops, from insects are known. Traditionally this has been done by spraying the crops with large amounts of pesticide. However, the widespread use of chemical pesticides has led to insects developing resistance to these compounds. Thus, either larger amounts of these chemicals have to be applied, or more potent pesticides must be used in order to achieve the desired level of pest control. Traditional methods of crop spraying also have the disadvantage that the pesticides kill both beneficial and harmful insects as they are not species specific. In addition to the hazards to the environment, there are also dangers involved to the farmer who has to spray the pesticides onto the crops. These dangers include the danger of inhaling or dermal absorption of the spray.

Other methods of pest control include applying powders to a specific site at which the pest is known to be present. There are a number of limitations associated with applying pesticides in a loose powder format. Typically such methods are only economical to use in small areas of pest infestation. As such their use is more suited to home and garden discrete application and not to the important broadacre pest control markets, particularly agriculture and forestry. Also, direct application of loose powders to the environment, such as a by puffing or dusting, can be difficult and dangerous. For example, powders may easily be blown away, and inhalation of such powders is hazardous to the user. Furthermore, powders may easily be washed away, particularly in outdoor environmental conditions.

It is an object of the present invention to address at least some of the disadvantages of prior art.

Accordingly, there is provided a compact comprising particles and an active agent selected from a pesticide, including insecticides, acaricides and fungicides, herbicides, a plant nutrient, a fertiliser, an arthropod attractant such as a semiochemical, a semiochemical, a food or protein bait, and including mixtures of two or more thereof.

According to another aspect of the present invention there is provided the use of the compact as defined herein, wherein the active agent is an arthropod attractant, to attract an arthropod by the controlled release of the arthropod attractant.

According to another aspect of the present invention there is provided a method of applying the compact as defined herein to a substrate, the method comprising applying sufficient force to the compact such that at least some of the particles adhere to the substrate.

According to a further aspect there is provided a method of applying the compact as described herein to a holder and/or cradle, the method comprising placing, inserting and/or partially inserting the compact on to and/or into a holder and/or a cradle such that at least a part of the compact is retained in and/or on the holder and/or cradle.

Each aspect as defined herein may be combined with any other aspect or aspects unless clearly indicated to the contrary. In particular any feature indicated as being preferred or advantageous may be combined with any other feature or features indicated as being preferred or advantageous.

The present invention will now be described further, by way of example only, with reference to the following figures, in which.

The compact of the present invention has the advantage that it may be applied to crops to protect them from arthropods. It may also usefully be applied inside buildings, for example in warehouses, on beams and on crates. It may also be suspended in a holder by a hanging means. For example, it may be suspended from a wall or a tree branch. The present invention is of particular use for controlling arthropods in areas where spraying and fumigating would not be appropriate, for example, in areas where food is stored, or in areas where people or animals inhabit or frequent.

The compact has a number of advantageous properties which make it desirable for use in arthropod control. The compact may be cheaply manufactured, and does not require excessive amounts of packaging. It is easy to transport and can readily and safely be applied to a target area. Furthermore, the compact of the present invention may quickly and safely be applied to a target site and avoids the disadvantages of having to spray a pesticide on to a target area or crop.

As used herein the term "compact" is used to describe a solid produced by confining particles, with or without a binder, and compressing them.

As used herein the term "particles" includes particulates and powders. Compression of the particles together forms the compact. The particles are held together in the compact sufficiently strongly to allow the compact to remain substantially intact during storage and transport. However, the compact is sufficiently friable for arthropods to pick up particles from the compact whilst it is still compressed. It may also be sufficiently friable to allow the compact to be crushed upon application of pressure by, for example, a thumb. However, the compact is sufficiently compressed so that it may also be inserted into a hanger by means of suitable pressure without, or substantially without, breaking the compact. Preferably the compact is sufficiently compressed so that it may be shipped in packaging without, or substantially without, being damaged.

The individual particles which form the compact act as carriers of an active agent.

Typically the compact comprises at least 80%, at least 90%, at least 95% or at least 98% by weight of particles based on the total weight of the compact.

Preferably, at least 70% by weight of particles in the compact will have a volume mean diameter of 50 microns or less, 20 microns or less, or 10 microns or less. More preferably, at least 80%, or at least 90% by weight of particles in the compact will have a volume mean diameter of 50 microns or less, 20 microns or less, or 10 microns or less. More preferably still, at least 90% by weight of particles in the compact will have a volume mean diameter of 50 microns or less, 20 microns or less, or 10 microns or less. In one preferred embodiment of the present invention, at least 70%, more preferably at least 80%, more preferably still at least 90% by weight of the particles in the compact have a volume mean diameter of from 10 to 30 microns, more preferably from 15 to 20 microns.

The volume mean diameter of the particles is measured using a dry powder laser diffraction particle size analyser such as the Malvern Mastersizer or Sympatec Helos series instruments. A suitable quantity of dry particles is placed into a vibratory feed hopper of such instrument and blown into and through the flow path of the lasers. The volume mean diameter of the particles is thereby calculated.

Particles suitable for use in the present invention include waxes and particulate solids minerals, such as calcium carbonate, mica, talc, kaolin, bentonites, clays attapulgite, pyrophyllite, wollastonite, silica, feldspar, sand, quartz, chalk, limestone, precipitated calcium carbonate, diatomaceous earth and barites. Mixtures of two or more thereof may be used.

Preferably, the particles will be hydrophobic. The particles may comprise a hydrophobic coating, such as a stearic acid coating. Other suitable hydrophobic coatings will be known in the art.

In a preferred embodiment the particles comprise wax. Preferably, the wax is selected from carnauba wax, candelilla wax, microcrystalline wax, shellac wax, castor wax, ouricury wax, rice bran wax, paraffin wax, beeswax, lanolin, bayberry wax, sugar cane wax, ozocerite, ceresin wax, montan wax, and including mixtures of two or more thereof. Synthetic waxes may also be used, such as Shell HMP wax and Sasol Wax. In a preferred embodiment the particles comprise carnauba wax One of the advantages of the compact of the present invention comprising wax is that the wax(es) may be chosen to have the desired release rate of the active agent. Furthermore, the properties of wax, such as its hydrophobic nature, are advantageous. Moreover, typically wax is biodegradable so that the compact does not need to be collected after use and subsequently disposed of.

Preferably, the compact comprises at least 80% by weight of wax based on the total weight of the compact. More preferably, the compact comprises at least 90% by weight of wax based on the total weight of the compact. More preferably still, the compact comprises at least 95% by weight of wax based on the total weight of the compact Particles comprising wax are particularly preferred because they allow the slow release of the active agent over a given time period. Preferably, the compact of the present invention has a substantially zero order release rate of the active agent.

The term "zero-order release rate" as used herein means a substantially constant release rate of the active agent from the compact independent of the loading. Thus, once equilibrium has been reached, a plot of the mass of active agent released versus time is linear.

Preferably, the compact of the present invention has a substantially zero order release rate of the active agent from the compact for at least 30 days, 50 days, 60 days, 70 days, 80 days, more preferably at least 90 days, 100 days, 110 days, most preferably at least 120 days.

Waxes suitable for use in the present invention are readily available. Carnauba Wax, for example, is a naturally derived plant wax, obtained from the leaves of a palm tree known as *Copernica cerifera*. Typically carnauba wax contains esters of fatty acids (80-85%), fatty alcohols (10-15%), acids (3-6%) and hydrocarbons (1-3%). Specific for carnauba wax is the content of esterified fatty diols (about 20%), hydroxylated fatty acids (about 6%) and cinnamic acid (about 10%). Cinnamic acid, an antioxidant, may be hydroxylated or methoxylated.

Paraffin waxes with different congealing points may be used to affect the release rate of pheromone from the compact formulation. Typical congealing points for the paraffin waxes used in the present invention are from 52 to 54° C., from 54 to 56° C. and from 64 to 66° C.

There are a number of advantages associated with using carnauba wax in the compact. These include its high melting point, which at 78-85° C. is among the highest melting point of any natural wax. This may be particularly important given that field temperatures can reach exceptionally high temperatures, particularly in the US, South America, Africa and Australasia. The high melting point of carnauba wax means that the wax will be substantially unaffected by these high temperatures. Carnauba wax also has the advantage that its make up includes natural antioxidants which help to protect active agents associated therewith, and in particular dispersed or dissolved therein, from UV degradation.

In a preferred embodiment, the compact comprises carnauba wax and paraffin wax. The rate of release of an active agent from paraffin wax is typically faster than the rate of release from carnauba wax. Thus, by varying the relative percentage of the two waxes, the release rate properties of the compact may be varied. Furthermore, as paraffin wax is not as hard as carnauba wax, the addition of paraffin wax helps to bind the compressed wax particles in the compact. Additionally, the malleable nature of the paraffin wax aids the adhesion of the compact onto a target substrate such as a tree, fence post, or split cane.

The weight ratio of the carnauba wax to paraffin wax may be in the range of from 99:1 to 1:99, more preferably from 50:1 to 1:50, or from 10:1 to 1:10, more preferably still from 5:1 to 1:5, and most preferably 2:1 to 1:2. Preferably in the compact of the present invention the weight ratio of the carnauba wax to the paraffin wax is 99:1, 50:1, 25:1, 20:1, 10:1, 5:1, 2:1, 1:1, 1:2, 1:5, 1:10, 1:20, 1:25; 1:50 or 1:99.

In one embodiment of the present invention, the compact comprises mixtures of particles, wherein the particles are formulated from more than one wax (i.e. from wax blends), for example from carnuba wax and paraffin wax.

In one aspect of the present invention the compact comprises:

(i) particles associated with at least a first active agent, and optionally a flow agent, wherein the particles comprise a first wax and a second wax; and (ii) particles associated with at least a second active agent, and optionally a flow agent, wherein the particles comprise a third wax and a fourth wax;

wherein the first, second, third and fourth wax are independently selected from carnauba wax, candelilla wax, microcrystalline wax, shellac wax, castor wax, ouricury wax, rice bran wax, paraffin wax, beeswax, lanolin, bayberry wax, sugar cane wax, ozocerite, ceresin wax, montan wax, synthetic waxes and including mixtures of two or more thereof; and wherein the first active agent is the same or different to the second active agent.

Preferably the weight ratio of the first wax to the second wax in the particles associated with the first active agent are in the range of from 99:1 to 1:99, more preferably from 50:1 to 1:50, or from 10:1 to 1:10, more preferably still from 5:1 to 1:5, and most preferably 2:1 to 1:2. Preferably the weight ratio of the first wax to the second wax is 99:1, 50:1, 25:1, 20:1, 10:1, 5:1, 2:1, 1:1, 1:2, 1:5, 1:10, 1:20, 1:25; 1:50, 1:99, 75:25 or 25:75.

Preferably the weight ratio of the third wax to the fourth wax in the particles associated with the second active agent are in the range from 99:1 to 1:99, more preferably from 50:1 to 1:50, or from 10:1 to 1:10, more preferably still from 5:1 to 1:5, and most preferably 2:1 to 1:2. Preferably the weight ratio of the third wax to the fourth wax is 99:1, 50:1, 25:1, 20:1, 10:1, 5:1, 2:1, 1:1, 1:2, 1:5, 1:10, 1:20, 1:25; 1:50, 1:99, 75:25 or 25:75.

Preferably in this embodiment, the first wax is not the same wax as the second wax. Preferably the third wax is not the same wax as the fourth wax. The first wax may be the same as the third wax and/or fourth. The second wax may be the same as the third wax and/or fourth wax. Preferably, the release rate of the first active agent from the particles comprised of the first and second wax is different to the release rate of the second active agent from the blend of particles comprised of the third and fourth wax.

The compact of the present invention may comprise of two, three, four or more different blends of wax particles.

Preferably the first wax is carnauba wax and the second wax is paraffin wax. Preferably, the third wax is carnauba wax and the fourth wax is paraffin wax. In this embodiment, preferably the ratio of carnauba wax to paraffin wax in the particles associated with the first active agent, is different to the ratio of carnauba wax to paraffin wax in the particles associated with the second active agent.

Preferably, the weight ratio of carnauba wax to paraffin wax in the particles associated with the first active agent is the range of from 99:1 to 1:99, more preferably from 50:1 to 1:50. Preferably, the weight ratio of carnauba wax to paraffin wax in the particles associated with the first active agent is 75:25. Preferably, the weight ratio of carnbuba wax to paraffin wax in the particles associated with the second active agent is the range of from 99:1 to 1:99, more preferably from 50:1 to 1:50. Preferably the weight ratio of carnbuba wax to paraffin wax in the particles associated with the second active agent is 25:75.

In this aspect of the present invention, preferably the wax blends are prepared, and associated with the required active agent. The formulations are then micronised, mixed with blends of other formulations and then compressed into compacts. Alternatively, the formulations consisting or comprising of different blends may be compressed individually to form a portion of the desired compact. The compressed blends may then be compressed together to form the final compact. One advantage of mixing the formulations of the different blends prior to compression is that the different blends can be dispersed throughout, or substantially throughout the compact. If the release rates of the formulations are different, such a formulation allows for different release rates within the compact. Advantageously, the compact may comprise particles having a combination of faster and slower release rates.

Typically the compact of the present invention will comprise a flow agent. The addition of a flow agent assists in the manufacturing of the compact, making the particles easier to pour into a compression or tabletting mould. Additionally, the flow agent aids the friability of the compact if it is applied to a target substrate. Suitable flow agents include silica based flow agents, for example, Sipernat D17®, which is available from Degussa. Other additives such as glyceryl monostearate may also be used as flow agents. Typically, suitable flow agents will be hydrophobic.

Preferably, the compact comprises from 0.01% to 10% by weight of flow agent based on the total weight of the compact. More preferably, the compact comprises from 0.01% to 5%, or from 0.25 to 5% by weight of flow agent based on the total weight of the compact.

Typically the compact will have a density of from 0.1 to 3 $gcm^{-3}$, more preferably from 0.2 to 2 $gcm^{-3}$, more preferably still from 0.3 to 1 $gcm^{-3}$.

Preferably, the compact comprises from 0.001% to 30% by weight of an active agent based on the total weight of the compact. More preferably, the compact comprises from 0.01% to 5%, or from 1 to 5% by weight of an active agent based on the total weight of the compact.

The active agent may be dissolved in or associated with the particles of the compact. In one embodiment at least some of the particles may be at least partially coated in the active agent. Additionally, or alternatively, at least some of the particles may be fully coated in the active agent.

The term "semiochemical" as used herein is meant a chemical or specific blend of chemical substances which can elicit a specific behavioural response from an organism. Semiochemicals may be further divided into pheromones and allelochemicals. These terms are well known in the art and as used herein include synthetic chemicals or synthetic blends of chemical substances that are not produced naturally but which mimic the naturally occurring semiochemicals.

Suitable semiochemicals for use in the present invention include, but are not limited to insect semiochemicals comprising of single or multi-component blends of aliphatic compounds comprising chains of up to 20 carbon atoms, and containing up to three double bonds, epoxides and/or ketones. It will be understood that suitable single or multi-component blends of aliphatic compounds comprising chains of more than 20 carbon atoms, and containing up to three double bonds, epoxides and/or ketones may also be used in the present invention. The aliphatic chain may also contain one or more aliphatic branches and a terminal oxygenated functionality, typically an alcohol, formate, acetate, ester, aldehyde or nitrate.

Suitable sex pheromones include, but are not limited to:
Alcohols:
Hexan-1-ol; (Z)-3-hexen-1-ol; decan-1-ol; dodecan-1-ol; (Z)-8-dodecen-1-ol; (E)-8-dodecen-1-ol; (E)-9-dodecen-1-ol; (E,Z)-7,9-dodecadien-1-ol; (E,E)-8,10-dodecadien-1-ol; (E,Z)-8,10-dodecadien-1-ol; (Z,E)-8,10-dodecadien-1-ol; tetradecan-1-ol; (Z)-9-tetradecen-1-ol; (Z)-11-tetradecen-1-ol; (Z,E)-9,12-tetradecadien-1-ol; hexadecan-1-ol; (Z)-11-hexadecen-1-ol; octadecan-1-ol; (E,Z)-2,13-octadecadien-1-ol; eicosan-1-ol.
Aldehydes:
Hexan-1-al; nonan-1-al; (E,E)-8,10-dodecadien-1-al; tetradecan-1-al; (Z)-9-tetradecen-1-al; (Z)-11-tetradecen-1-al; (Z,E)-9,12-tetradecadien-1-al; hexadecan-1-al; (Z)-7-hexadecen-1-al; (Z)-9-hexadecen-1-al; (Z)-11-hexadecen-1-al; (E)-11-hexadecen-1-al; (Z)-12-hexadecen-1-al; octadecan-1-al; (E)-2-octadecen-1-al; (Z)-13-octadecen-1-al; (E,Z)-2,13-octadecadien-1-al.
Acetates:
(Z)-3-hexen-1-yl acetate; decan-1-yl acetate; dodecan-1-yl acetate; (Z)-7-dodecen-1-yl acetate; (E)-7-dodecen-1-yl acetate; (E)-8-dodecen-1-yl acetate; (Z)-8-dodecen-1-yl acetate; (E)-9-dodecen-1-yl acetate; (Z)-9-dodecen-1-yl acetate; (E,E)-7,9-dodecadien-1-yl acetate; (E,Z)-7,9-dodecadien-1-yl acetate; (Z,E)-7,9-dodecadien-1-yl acetate; (Z,Z)-7,9-dodecadien-1-yl acetate; (E,E)-8,10-dodecadien-1-yl acetate; (E,E)-7,9,11-dodecatrien-1-yl acetate; (E,E)-7,9,11-dodecatrien-1-yl acetate; (Z,E)-7,9,11-dodecatrien-1-yl acetate; (Z,Z)-5,9-tridecadien-1-yl acetate; (E,Z)-5,9-tridecadien-1-yl acetate; tetradecan-1-yl acetate; (Z)-9-tetradecen-1-yl acetate; (E)-9-tetradecen-1-yl acetate; (Z)-11-tetradecen-1-yl acetate; (E)-11-tetradecen-1-yl acetate; (Z,E)-9,11-tetradecadien-1-yl acetate; (E,E)-9,11-tetradecadien-1-yl acetate; (Z,E)-9,12-tetradecadien-1-yl acetate; hexadecan-1-yl acetate; (Z)-11-hexadecen-1-yl acetate; (E)-11-hexadecen-1-yl acetate; octadecan-1-yl acetate; eicosan-1-yl acetate.

Miscellaneous:

Butyl hexanoate; (Z,Z,Z,Z)-7,13,16,19-22-isobutyrate; (Z)-7,10-acetoxy-7-hexadecen-1-ol; (Z)-7,8-epoxy-2-methyloctadecane; (Z)-7,8-epoxy-2-methyloctadecane; (Z)-7,8-epoxy-2-methyloctadec-17-ene; 1,3,8-trihydroxy-6-methyl-anthracene-9,10-dione; 2-methyl-(Z)-7-octadecene; 2-phenylacetaldehyde.

The semiochemical used in the present invention may be designed to attract arthropods, and in particular insects and preferably pest insects. The insects may include pests encountered in agriculture, horticulture, forestry and public health. Such insects include (among others) ants and termites, lepidopteran pests (moths and butterflies), flies (e.g. fruit flies, tsetse flies, biting flies, houseflies and mosquitoes), cockroaches, coleopteran pests (e.g. beetle pests of forestry plantations).

In particular, but without limitation, the semiochemical of the present invention may be chosen to attract *Cydia pomonella, Tinea pellionella, Tineola bisselliella, Grapholita molesta, Lobesia botrana, Chilo suppressalis, Plodia interpunctella, Ephestia elutella, Cadra cautella, Euproctis chrysorrhoea, Plutella xylostella, Helicoverpa armigera, Archips podana, Lymantria dispar, Heliothis virescens, Spodoptera exempta, Spodoptera frugiperda, Spodoptera litura, Epiphyas postvittana, Adoxophyes orana, Eupoecilia ambiguella* and *Scirpophaga incertulas* or combinations of semiochemicals may be used in the present invention to attract complementary species affecting the same crops such as Codling moth & Oriental Fruit moth (*Cydia pomonella* and *Grapholita molesta*) in apples and pears and European Grapevine moth & European Grape Berry moth (*Lobesia botrana* and *Eupoecilia ambiguella*) in grapes/vineyards.

The specific amount and type of semiochemical used in the compact of the present invention is chosen such that the semiochemical is released from the compact in sufficient quantities to act as a lure or attractant to a specific arthropod, and in particular an insect, more preferably an insect pest.

It will be understood that more than one semiochemical may be present in the compact.

Preferably, the compact comprises from 0.001% to 30% by weight of a semiochemical based on the total weight of the compact. More preferably, the compact comprises from 0.01% to 5%, or from 1 to 5% by weight of a semiochemical based on the total weight of the compact.

Other arthropod attractants may be used in the present invention, in addition to, or instead of semiochemicals. For example, food and protein baits may be used.

By the term "pesticide" as used herein is meant any substance which can be used in the control of agricultural, natural environmental, public health, stored product and domestic pests, such as insects. These include, but are not limited to insecticides, chemosterilants, anti-microbial agents, acaricides, ovicides, larvicides, insect growth regulators, fungicides, fungi, viruses and their metabolites, bacteria, bacterial toxins and their metabolites, essential oils, larvicides, nematodes or any combination thereof.

Preferably, the compact comprises from 0.001% to 30% by weight of a pesticide based on the total weight of the compact. More preferably, the compact comprises from 0.01% to 5%, or from 1 to 5% by weight of a pesticide based on the total weight of the compact.

A variety of herbicides, fertilisers, and plant nutrients may be used in the compact. Plant nutrients include, but are not limited to nitrogen, magnesium, calcium, boron, potassium, copper, iron, phosphorous, manganese, and zinc. Preferred examples include highly systemic herbicides, such as glyphosate. Preferred plant nutrients include those which are readily absorbed into foliage, trunks, branches or similar.

A variety of additives may be incorporated into or associated with the particles of the present invention. These additives may be chosen such that they change and/or enhance the physical characteristics of particles. For example, wherein the particles comprise wax and the active agent is a semiochemical, it may be desirable to alter the release characteristics of the semiochemical from the wax. Various additives may therefore be added in order to alter the rate and/or amount of semiochemical released. They may also act, for example, to protect the wax composition against destruction by weather conditions, etc.

In one embodiment of the present invention the compact comprises at least one additive. More preferably the additive comprises a UV blocker, a colourant, a plasticizer, an antimicrobial, an antioxidant, a wildlife repellent or a mixture thereof.

Ultraviolet blockers, such as beta-carotene or p-aminobenzoic acid may be present in the compact. Ultraviolet blockers are useful for protecting active agents, such as semiochemicals from light degradation.

Colourants such as optical brighteners and commercially available colourants, including suitable food colourants may be included in the compact. The addition of a colourant to the compact may have a number of advantages. For example, when the compact is placed in an area in which food is prepared or served, it may be desirable to dye the compact blue for marketing or for health and safety reasons. Applying compacts of different colours to a substrate, and in particular to a fruit tree, may also have that advantage that if a second application is required, it is easy to distinguish between the two applications of the compacts which have different colours. Furthermore, some arthropods are attracted to particular colours and, as such, colorants could be used to aid attraction of the target arthropod to the compact. Alternatively, it may be desirable to add colourants such that the compact blends in with background colours, thereby decreasing the attraction of birds or other wildlife to the compact.

Plasticisers, such as glycerine or soy oil may be included when the particles comprise wax. The presence of plasticizers typically effects the physical properties of the wax and may extend its resistance to environmental degradation and may also alter semiochemical release rates.

Antimicrobials, such as potassium sorbate, nitrates, nitrites, and propylene oxide, may be present in the compact. Antimicrobials may protect the semiochemical from microbial degradation.

Antioxidants, such as vitamin E, BHA (butylated hydroxyanisole), BHT (butylated hydroxytoluene) and other antioxidants may be present in the compact. These antioxidants may help to protect the active agent from degradation. Antioxidants may be present in the compact in a 1:1 weight ratio with the active agent. However, it will be understood that other suitable amounts may be used.

The inclusion of wildlife repellents may be useful in order to repel unwanted wildlife from the compact. Suitable wildlife repellents are well known in the art and include, for example, Bitrex.

In one embodiment of the present invention, the compact is at least partially encapsulated by a coating. Preferably, the compact is fully encapsulated by a coating.

It may be advantageous to form a coating, or a partial coating, on the compact in order to help the compact maintain its shape and consistency, whilst still maintaining its friability. The coating may be designed such that it may be removed by peeling. Alternatively, or additionally, the coating may be designed to dissolve away, when, for example, it is exposed to rain, leaving the particles associated, with the active agent of the compact exposed to the surrounding environment.

It will be understood that when the compact is encapsulated by a coating, or is at least partially encapsulated by a coating, the particles which form the compact will still be friable.

The coating may comprise a film forming polymer, a wax, or a glue. Suitable film forming polymers include, but are not limited to cellulose derivatives, such as carboxymethylcellulose, hydroxyethylcellulose, cetylcelluolose, hydroxypropylcellulose, hydroxypropylmethyl cellulose, hydroxyethylmethyl cellulose, methylcellulose or mixtures of two or more thereof.

Suitable waxes for coating the compact preferably have a melting point of less than the melting point of waxes comprised within the compact. Preferably, waxes used for coating the compact include, but are not limited, to waxes having melting points in the range of from 30 to 60° C., more preferably, in the range of from 40 to 55° C. Such wax coatings may be applied without melting the waxes of the compact.

It may be advantageous to include a surfactant in the wax or the film-forming polymer for use in coating the compact. Suitable surfactants include, but are not limited to sodium dodecyl sulphate, benzalkonium chloride, cocamidopropyl betaine, octanol, biological compounds such as phospholipids, cholesterol, glycolipids, fatty acids, bile acids, saponins, Lauric acid and myristic acids.

The compact may be encapsulated, or partially encapsulated, with one or more coating layers. Methods of applying the coating include spraying and dipping.

Preferably, the coating/and or partial coating is applied to the compact after compaction. This allows the compact to maintain its consistency and friability. Preferably, the coating with have an average depth of less than 2 mm, more preferably less than 1 mm. At least partially encapsulating the compact may have the further advantage of increasing the storagability of the compact by reducing the amount of active agent lost to the atmosphere before the compact is crushed, applied to a hanger or applied to a substrate.

In one aspect of the present invention there is provided the use of the compact as defined herein, wherein the active agent is an arthropod attractant, to attract an arthropod by the controlled release of the arthropod attractant. Preferably, the arthropod attractant is a semiochemical.

When the compact comprises an arthropod attractant, and in particular a semiochemical, it may advantageously be used in mating disruption techniques, or lure and kill/sterilisation techniques.

In traditional mating disruption a target area is 'flooded' with pheromone from a target species. The aim is to release sufficient quantities of pheromone to create a generally homogenous "fog" of pheromone in the target area during the period when the target insect is at its adult stage. The high levels of sex pheromone in the target area reduce the ability of the male to find the female (or vice versa) thereby reducing successful mating or delaying mating. Such delays reduce the fecundity or fertility of the female and reduce the viability of the eggs laid. In this way the mating of the target is disrupted and the number of viable offspring produced is reduced.

In one embodiment of the present invention a target arthropod, preferably an insect, more preferably a pest insect, may be attracted to the compact comprising a semiochemical. Upon contact of the arthropod with the compact, the semiochemical and/or particles associated with the semiochemical become attached to the arthropod and are retained thereon. The semiochemical and/or particles attached to the target arthropod thereafter reduces the ability of the male to find females with whom they can mate due to the proximity and excess of sex pheromone released from the attached particles. The sex pheromone and/or particles formulated with the sex pheromone may also be transferred to males of the same species upon interaction. In this way mating is disrupted. The applicants have called this mating disruption by an auto-confusion technique. This method of mating disruption has the advantage that it is not necessary to place enough compacts in the target area to create a fog. Instead, the target arthropod is attracted to the compact itself. This has the advantage that lower doses of semiochemicals are needed in order to control the arthropod population. A particular advantage of using the compact of the present invention over previously known mating disruption techniques and auto-confusion techniques is that the compact is easy and quick to apply, and avoids the need for dispensers and traps. Such dispensers and traps are time consuming to make and put in place in a target site. After use they must also be collected and disposed of. In contrast to this the compact is easy to position in a target area and need not be removed after its useful life has finished. Where a hanger is used outdoors, it will ideally be made from a biodegradable material so that it will not have to be removed after its useful life has ended. Where a hanger is used indoors, it will ideally not be biodegradable so as to make it reusable. Ideally it will incorporate metal detectable material. Warehouses in which foodstuffs are processed or stored use metal detectors to ensure that the food products are not contaminated with metal. As such, use of a metal detectable material in the hanger/holder of the present invention, when used indoors, will make it detectable if it finds it way into the foodstuffs stored or processed in the building.

In addition to mating disruption by auto-confusion, the action of attracting the arthropod to the compacts means that the compacts act as false lures thereby diverting the male of the species away from females and thereby either preventing or delaying mating, such delay resulting in reduced female fertility by the time of mating.

In another embodiment the compact comprises a semiochemical, and/or an attractant such as a food or protein bait, and the compact is used to act as a lure, which may be placed in a dispenser or a trap. The semiochemical and/or other attractant is released from the compact, attracting arthropods towards the lure.

In a further embodiment of the present invention for use in lure and kill techniques the compact preferably comprises at least one arthropod attractant, such as a food or protein bait, or a semiochemical, and at least one pesticide. The target insect is attracted to the compact by the semiochemical, where it comes into contact with the compact. Upon contact with the compact at least some of the active agent, preferably a pesticide, is transferred from the compact to the target insect. Preferably, upon contact of the target arthropod with the compact at least some of the particles which form the compact adhere to the arthropod. In this way the particles may be subsequently transferred from one arthropod to another. Contact of the arthropod with the pesticide results in it being killed or sterilised.

In another embodiment of the present invention for use in lure and kill techniques, the compact may comprise an arthropod attractant, which is preferably a semiochemical, to which a target arthropod is attracted. In this embodiment the pesticide source may not be associated directly with the compact, but instead, or additionally, may be located within the vicinity of the compact, such that attraction of the arthropod to the attractant in the compact encourages the arthropods to be attracted to the pesticide source.

The compact of the present invention may have the shape of a cylinder, pyramid, cuboid, parallelepiped, tube, column, disc, or any other suitable polyhedron. However, it will be understood that the compact may take a variety of shapes and sizes.

The inventors have found that it is particularly preferred when the compact is formed into a cylindrical shape. This shape has the advantage that it is easy to manufacture. Moreover, cylindrical compacts have the advantage that they do not have right angled edges. Such edges tend to be easily broken during transport and storage of the compact.

In one embodiment the compact is in the form of a pellet. Preferably, the total weight of the pellet is less than 5 g, more preferably, the total weight of the pellet is less than 3 g, or less than 1 g.

In one aspect of the present invention there is provided a method of applying the compact as described herein to a substrate, the method comprising applying sufficient force to the compact such that at least some of the particles adhere to the substrate.

In one embodiment, the force may be applied by a human thumb. In this embodiment, it is preferable for the compact to be of such a size that it can easily be applied by a thumb of a human. For example, it is preferred that the pellet has dimensions of less than 2 cm$^3$, preferably less than 1 cm$^3$.

Alternatively, the compact may be of suitable shape and size such that it can be fired or propelled on to a substrate. This may be particularly advantageous when the substrate on which the compact is to be applied is out of reach of a human, or otherwise difficult to get to.

The compact of the present invention may be applied, for example, to horticultural crops such as actively growing agricultural crops, fruiting agricultural crops, actively growing ornamental crops, fruiting ornamental crops and the products thereof, and other surfaces pests infest such as man-made structures and stored grains/fruits/nuts/seeds. Specific examples include fruits, vegetables, trees, flowers, grasses and landscape plants and ornamental plants. Particularly preferred plants include apple trees, pear trees, peach trees, plum trees, lemon trees, grapefruit trees, avocado trees, orange trees, apricot trees, walnut trees, raspberry plants, strawberry plants, blueberry plants, blackberry plants, boysenberry plants, corn, beans including soybeans, squash, tobacco, roses, violets, tulips, tomato plants, grape vines, pepper plants, wheat, barely, oats, rye, triricale, and hops. Man-made structures to which the compact may be applied include buildings, storage containers, dwellings made of various materials such as plastics, wood, stone, cement, and metal. The compact of the present invention may also be applied to fences, fence poles, crop supporting wire and canes.

The compact may comprise a hanging means. The hanging means may be a wire or thread. The wire or thread may comprise a loop from which the pellet may be hung.

In another embodiment, the compact may be suspended from a target site, such as a tree, or building structure, by the use of a cradle. The compact may be crushed onto the cradle. Alternatively, or in addition, the compact may simply be placed in the cradle or partially encapsulated by the cradle.

Figure 1:
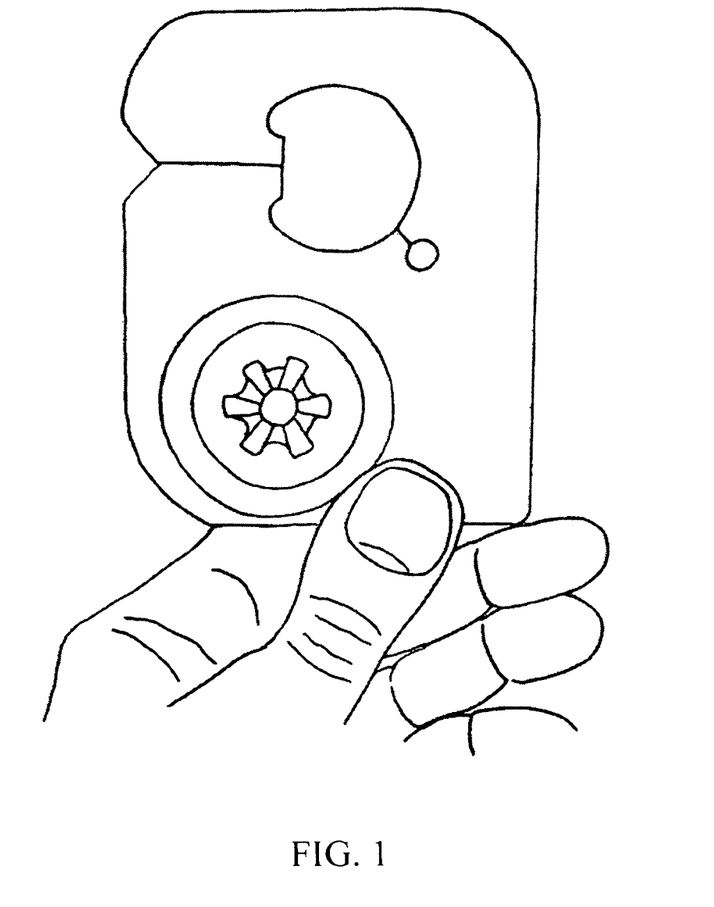
FIG. 1 is a line drawing of a compact of the present invention retained in a holder. This drawing shows the reverse side of the holder.
Figure 2:
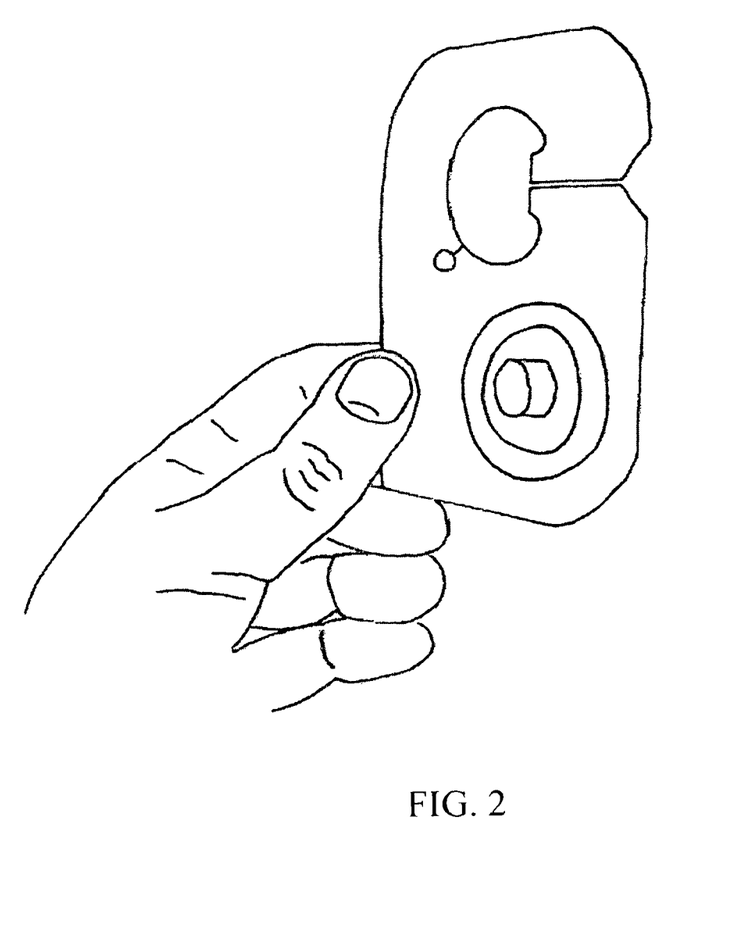
FIG. 2 is a line drawing of a compact of the present invention retained in a holder. This drawing shows the front side of the holder.
Figure 3:
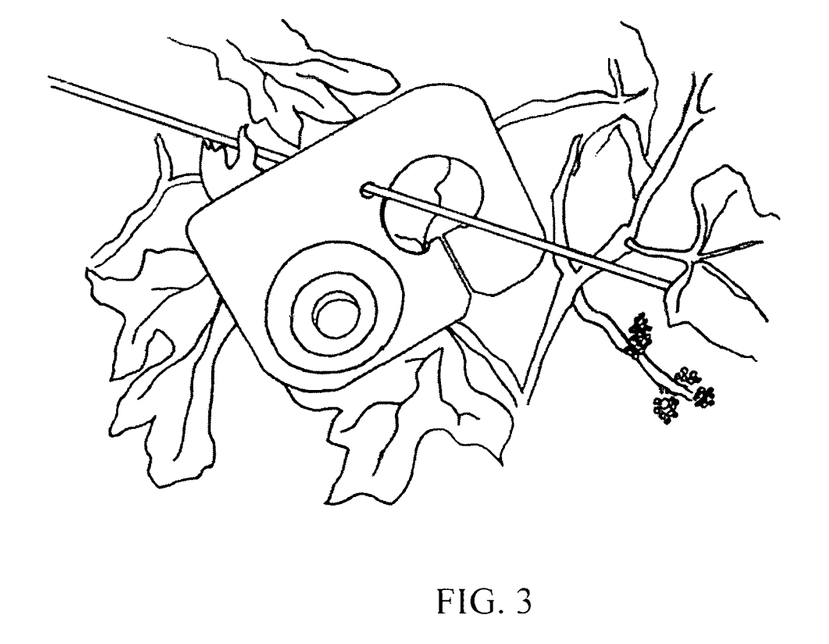
FIG. 3 is a line drawing of a compact of the present invention retained in a holder, where the holder is hanging in a tree.
Figure 4:
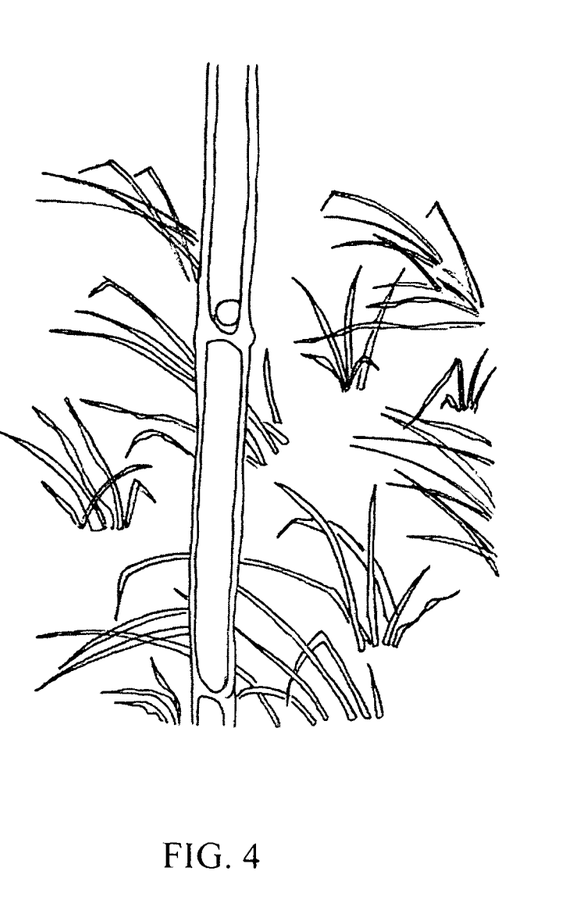
FIG. 4 is a line drawing of a compact of the present invention crushed onto bamboo.

The compact as described herein may be placed, inserted and/or partially inserted onto and/or into a holder and/or a cradle such that at least a part of the compact is retained in and/or on the holder or cradle. It may be inserted and/or partially inserted into a hole, recess or retainer formed in or on the holder and/or cradle. The holder and/or cradle preferably has a hanging means, so that it may be easily applied to a target site, for example, a tree branch, or a part of a building. FIGS. 1 and 2 show a compact of the present invention retained in a holder. FIG. 3 shows a compact of the present invention retained in a holder, where the holder is hanging from a tree.

One or more compacts may be retained on one holder and/or cradle. Each compact may comprise an active agent specific for a particular insect. Alternatively, each compact may comprise an active agent which is specific for number of insects.

In one embodiment the present invention provides a holder and/or retainer comprising one or more compacts comprising active agents specific to the Codling moth (*Cydia pomonella*).

In another embodiment the present invention provides a holder and/or retainer comprising one or more compacts comprising active agents specific to the Oriental Fruit moth in peaches (*Grapholita molesta*).

In another embodiment the present invention provides a holder and/or retainer comprising one or more compacts comprising active agents specific to the Yellow Stem Borer moth in rice (*Scirpophaga incertulas*).

In another embodiment the present invention provides a holder and/or retainer comprising one or more compacts which comprise active agents specific to the Codling moth & Oriental Fruit moth in apples and pears (*Cydia pomonella* and *Grapholita molesta*).

In another embodiment the present invention provides a holder and/or retainer comprising one or more compacts which comprise active agents specific to the European Grapevine moth & European Grape Berry moth in grapes/vineyards (*Lobesia botrana* and *Eupoecilia ambiguella*).

In a further embodiment the present invention provides a holder and/or retainer comprising one or more compacts which comprise active agents specific to the Codling moth & Fruittree Tortrix moth in apples (*Cydia pomonella* and *Archips podana*).

Figure 5:
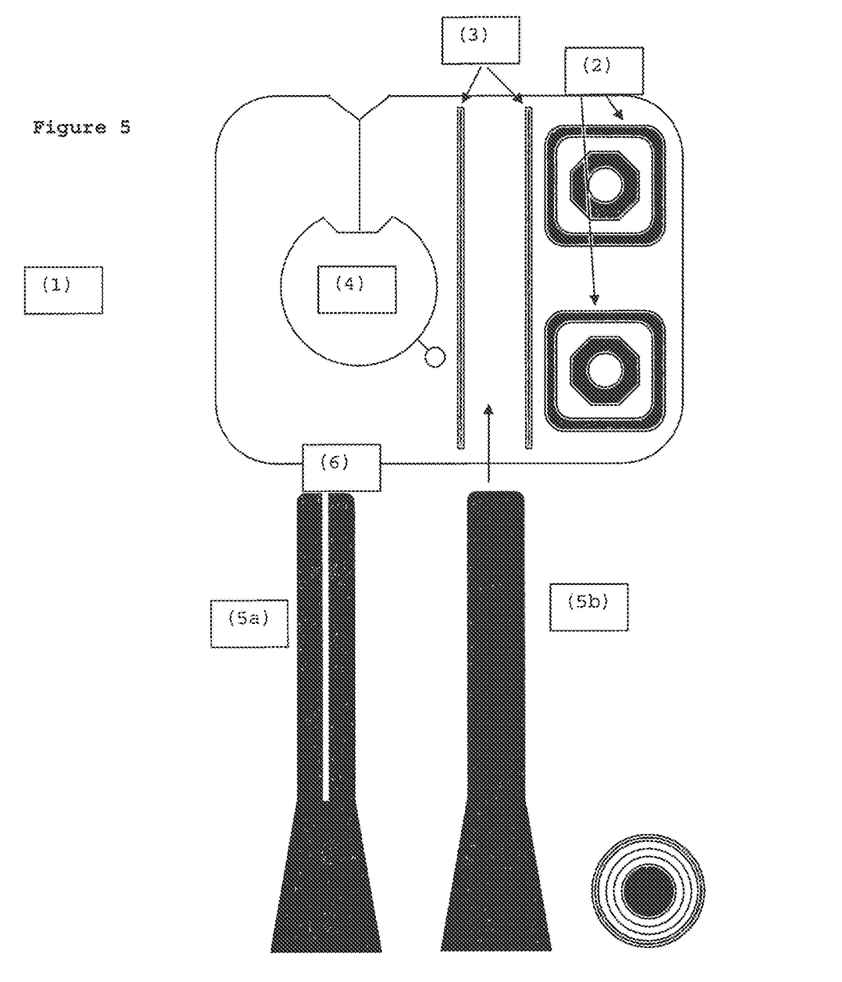
FIG. 5 is a schematic sketch of a holder for retaining a compact of the present invention. The Figure also shows a device for mounting the holder, in for example a tree.

An example of a holder which may be used for retaining the compact of the present invention is shown in FIG. 5. The holder (1) has two holes, or retainers (2). The holder may have one, two, three or more such holes or retainers. The hole or retainer (2) is designed such that the compact may be placed, inserted, and/or partially inserted into the hole or retainer (2), so that it is retained on or in the holder (1). The holder (1) may have ribs (3), or a means by which the holder (1) can easily be mounted in position, in for example a tree, or in a building, where it would be difficult to position the holder simply by hand. The holder may have a hanging means (4). In this example the hanging means (4) is a hole, through which, for example, a branch may be pushed. The hole allows the holder to be suspended in position. FIG. 5 also shows a Device (5) (side view (5a), front view (5b)) which enables the holder to be mounted in position. A side view of the device (5a) shows that the device may have a slit (6) which may interlock with the ribs (3) and enable the holder to be temporarily held by the device (5). The holder (1) can then be positioned, in for example a tree or a building. The device (5a, 5b) can then be removed from the holder (1), leaving it in place.

Preferably, the compact of the present invention will not fragment and lead to a substantial loss of particles during normal handling, storage, or transport. Preferably, less than 10% by weight of the particles will fragment from the main body of the compact during storage and transport, more preferably less than 5%, more preferably still less than 2% by total weight of the compact. Upon application of pressure by, for example, a human thumb, the compact will deform and may be crushed on to a substrate. An advantage of the compact of the present invention is that the particles on the surface of the compact, after application of the compact to a substrate, remain associated with the compact, such that they do not readily blow away, for example, in the wind, or in air conditioning. However, at least some of the particles of the compact are sufficiently loosely associated with the compact that upon contact with an arthropod, preferably at least some of the particles are transferred from the compact to the arthropod. In this way the active agent may be transferred to the arthropod.

The compact of the present invention may be crushed onto a substrate. For example, onto bamboo, as shown in FIG. 4. The bamboo may then be inserted into the ground in a rice paddy field. This may be of particular use for controlling yellow stem borer (*Scirpophaga incertulas*) in rice fields.

It will be understood, however, that the compact of the present invention may simply be placed at a target site, for example, on a plant, in a building, on a dispenser, or a tray, i.e. the compact need not be crushed onto a target site. An arthropod may be drawn towards the compact by including at least one arthropod attractant, such as a semiochemical in the compact. In this embodiment, it may be desirable to form the compact into a shape suitable for placing on a surface. Suitable shapes for this use include, a substantially flat tablet shape, a disc, loop/ring or any other suitable polyhedron.

In a further aspect of the present invention there is provided a method of preparing the compact as defined herein comprising providing the particles, exposing the particles to an active agent such that the active agent is associated with the particles; and compressing the particles associated with the active agent to form the compact.

Typically the force range of from 0.5 to 10 Newtons per square centimeter is applied to the particle surface to form the compacts of the present invention. Preferably the particles are compressed to a density of 0.5-2 grams per cm cubed.

As described above, two or more active agents may be used in the compact of the present invention (for example 3, 4, 5, 6 or 7 etc. active agents may be used). Such compacts may be prepared by mixing at least the first and second active agent together, and exposing particles to the mixture of active agents, and compressing the particles associated with the active agent to form the compact.

The present inventors have found that in some circumstances, when two semiochemicals for use in attracting two different target species are mixed prior to application to the particles, the subsequent efficiency of the compact at attracting target arthropods of one or both of the target arthropods to the compact is reduced compared to the efficiency of attracting the two target arthropods to two different compacts comprising the individual semiochemicals. Similar results have been observed when more than two semiochemicals are applied using a similar method. The present inventors have surprisingly found that this reduction in efficiency of attracting two different target arthropods species by the use of two different semiochemicals associated with the same particles in the compact can be reduced by formulating the compact in the following way. The compact is formulated with two different particles A and B. Particles A are associated with active agent A. Particles B are associated with an active agent B. The compact is then formed by compressing particles A, associated with active agent A, with particles B, associated with active agent B. Particles A and B may be of the same or different material. Preferably the compact formed in this way has a first region having a higher percentage of particles A associated with active agent A and a second region having a higher percentage of particles B associated with active agent B. Alternatively, the particles A and B, associated respectively with active agent A and B, may be mixed prior to forming the compact. In this case, the particles A and B may be substantially evenly distributed throughout the compact. It will be understood that the method described above may be applied wherein more than two active agent are present in the compact, and/or where more than one particle type or size is used in the compact.

The following Examples further illustrate the present invention.

EXAMPLE 1

A 1.2 g compact for attracting Codling Moths, *Cydia pomonella*, was formulated using the following ingredients:

10 mg of (E,E)-8,10-Dodecadien-1-ol (pheromone);

10 mg butylated hydroxytoluene; and a wax mixture comprising a weight ratio of 51:49 carnauba wax to paraffin wax.

EXAMPLE 2

A 1.1 g compact for attracting Yellow Stem Borer, *Scirpophaga incertulas*, was formulated from the following ingredients:

3 mg of 66% (Z)-11-Hexadecenal, 33% (Z)-9-Hexadecenal (pheromone); and a wax mixture comprising a weight ratio of 75:25 carnauba wax to paraffin wax.

EXAMPLE 3

Compact 1 (Exosex$^2$ CM applied at 180 units per hectare) was formulated from 1% pheromone (a 60:32:8 blend of E8E10-12OH:12-OH:14-OH), 0.5% flow agent, 19.5% paraffin wax and 79% carnauba wax. This powder was compacted into 1 g pellets.

Compact 2 (Exosex$^2$ CM applied at 90 units per hectare) was formulated from 2% pheromone (a 60:32:8 blend of E8E10-12OH:12-OH:14-OH), 0.5% flow agent, 19.5% paraffin wax and 78% carnauba wax. This powder was compacted into 1 g pellets.

In particular the powders were compacted in the following way: 50 g of formulated powder (including 0.5% flow-agent) was spread across 50 wells in a fly-press. Pins were then lowered into the wells at a force determined by a torque wrench attached to the press. The lower supporting wall under the wells was removed and the compacts were pushed through.

In a commercial apple orchard in Hawkes Bay, New Zealand the following 4 treatments were compared in the control of the Codling Moth, *Cydia pomonella*.

Treatment 1

180 units of Compact 1 (Exosex$^2$ CM) were applied per hectare with each compact containing 10 mg of active ingredient.

Treatment 2

90 units of Compact 2 (Exosex$^2$ CM) were applied per hectare with each compact containing 20 mg of active ingredient.

Treatment 3

1000 units of a registered pheromone alternative, Isomate, was applied per hectare. This treatment was applied only once.

Treatment 4

An IFP (Integrated Fruit Production) programme—insecticide controlled farmer's practice. This treatment involved 1×indocicarb and 3×tebufenocide sprays. This treatment is similar to IPM (Integrated Pest Management) in that it encourages other methods of control such as the use of insect growth regulators and biologicals methods rather than relying on numerous applications of hard chemicals such as organophosphates.

All plots were circa 2 hectares in size. Pheromone treatments were applied at biofix (the first flight of moths during the season) and the treatments 1 and 2 (Exosex$^2$ treatments) were re-applied approximately 60 days after the first application. The compacts of treatments 1 and 2 (Exosex$^2$ units) were applied by crushing the compacts directly into the top third of the trees. All pheromone treatments received 1 tebufenozide application. The IFP treatment (treatment 4) received 1 indoxacarb application and 3 tebufenozide applications.

Results (damage as % of infested apples):

| Product and dosage | Damage on trees | in bins | in packing line |
|---|---|---|---|
| Treatment 1: | | | |
| Exosex$^2$, 10 mg at 180 units/ha (1 spray) | 0 | 0.15 | 0 |
| Treatment 2: | | | |
| Exosex$^2$, 20 mg at 90 units/ha (1 spray) | 0.05 | 0.15 | 0 |
| Treatment 3: | | | |
| Isomate (1 spray) | 0 | 0.2 | 0.75 |
| Treatment 4: | | | |
| Chemical (4 sprays) | 1.8 | 0.2 | 0 |

New Zealand supply fruit to Taiwan, where Codling Moth is viewed as a serious threat which they do not wish to import. Therefore Taiwan have mandated that two extra checks on apples are performed Codling Moth to be undertaken prior to leaving New Zealand. One is an apple inspection that takes place in the fruit bins on the farm immediately after picking ("in bins" in the table above). This sample is 1000 fruit from 10 bins in each treatment and variety. The other additional independent assessment is performed in the packing house where all fruit is examined on the grading line as it is being packed and has to be reported ("in packing line" in the table above).

Additional note: An assessment of the time required to apply the pheromone products showed that placing 90-180 Exosex$^2$ units (including the second application) took 70% less time to apply than the alternative Isomate product. All pheromone treatments show very good efficacy and are acceptable to the grower.

EXAMPLE 4

Exosex$^2$ GVM-Lb compacts are formulated from 1% pheromone (E7Z9-12Ac), 0.5% flow agent, 19.5% paraffin wax and 79% carnauba wax. This powder was compacted into 1 g pellets.

In two commercial vineyards in Portugal two trials were performed to evaluate the efficacy of Exosex$^2$ GVM-Lb against the Grapevine moth, Lobesia botrana. In "Trial 1" Exosex$^2$ GVM-Lb was compared only to a registered pheromone alternative, Isonet with 750 units per hectare applied once during the season. In "Trial 2" Exosex$^2$ GVM-Lb was compared Isonet and also to a farmer's practice standard chemical insecticide programme. Exosex$^2$ GVM-Lb was tested with 180 units applied per hectare with each compact containing 10 mg of active ingredient. All plots were circa 2 hectares in size. Pheromone treatments were applied at biofix and the Exosex$^2$ treatments were re-applied approximately 60 days after the first application. Exosex$^2$ units were applied by crushing the compacts directly into the top third of the vines.

Results (% of bunches infested with the pest):

| Product and dosage | Trial 1 | Trial 2 |
|---|---|---|
| Assessment 1 (start of season) | | |
| Exosex$^2$ GVM-Lb | 0.33 | 0.67 |
| Isonet | 1.00 | 2.00 |
| Chemical treatment | — | 1.33 |
| Assessment 2 | | |
| Exosex$^2$ GVM-Lb | 0.67 | 0.67 |
| Isonet | 0.67 | 1.00 |
| Chemical treatment | — | 2.00 |
| Assessment 3 (end of season for Trial 2) | | |
| Exosex$^2$ GVM-Lb | 1.33 | 1.20 |
| Isonet | 2.33 | 1.40 |
| Chemical treatment | — | 1.80 |
| Assessment 4 (end of season for Trial 1) | | |
| Exosex$^2$ GVM-Lb | 4.00 | — |
| Isonet | 6.20 | — |
| Chemical treatment | — | — |

The results indicate efficacy at least as good as the alternative currently registered pheromone product.

EXAMPLE 5

Exosex$^2$ OFM compacts are formulated from 2% pheromone (a 92:8 blend of Z8-12Ac:E8-12Ac), 0.5% flow agent, 19.5% paraffin wax and 78% carnauba wax. This powder was compacted into 1 g pellets.

In a commercial peach orchard in Mendoza, Argentina a range-finder type trial was performed to attempt to optimise the ideal dose rate for the Exosex$^2$ OFM product against the Oriental Fruit Moth, Grapholita molesta. Exosex$^2$ OFM was formulated at 3 doses: 5 mg of active ingredient per unit, 20 mg per unit and 35 mg per unit. Each dose was applied at 120 units per hectare, 180 units per hectare and 240 units per hectare giving a total of 9 Exosex$^2$ OFM rates which were applied twice for the season and compared against a registered pheromone alternative, RAK with 750 units applied once for the season. Exosex² OFM treatments were applied twice, the second application 60 days after the first. An untreated area was also provided to determine the scale of the damage in the absence of any product to control the pest. Exosex² units were applied by crushing the compacts directly into the top third of the trees.

| Results | |
|---|---|
| Product and dosage | % damage |
| Exosex² 5 mg at 120 units/ha | 1.79 |
| Exosex² 5 mg at 180 units/ha | 1.88 |
| Exosex² 5 mg at 240 units/ha | 0.99 |
| Exosex² 20 mg at 120 units/ha | 1.07 |
| Exosex² 20 mg at 180 units/ha | 0.83 |
| Exosex² 20 mg at 240 units/ha | 2.09 |
| Exosex² 35 mg at 120 units/ha | 3.93 |
| Exosex² 35 mg at 180 units/ha | 2.47 |
| Exosex² 35 mg at 240 units/ha | 2.46 |
| RAK 750 | 1.19 |
| Untreated | 4.21 |

The results showed that the best dosage rate for Exosex² OFM was to use 180 units per hectare with each unit containing 20 mg of active ingredient. This treatment statistically performed equally as well as the alternative currently registered pheromone product. Exosex² OFM at this prevented more than 3% crop yield loss to the farmer over applying no preventative measures against the pest.

EXAMPLE 6

Exosex² YSB is formulated from 0.3% pheromone (a 3:1 blend of Z11-16Ald:Z9-16Ald), 0.5% flow agent, 20% paraffin wax and 79.2% carnauba wax. This powder was compacted into 1 g pellets.

In commercial rice paddies in Cherukupalli village, Guntur District, coastal Andhra Pradesh, India the following 4 treatments were compared during the control of the Yellow Stem Borer, *Scirpophaga incertulas* (Lepidoptera: Pyralidae): Exosex² YSB at 80 units applied per hectare with each compact containing 3.2 mg of active ingredient; A chemical treatment programme near the Exosex² treatment—near farmer's practice; A chemical treatment programme further away from the Exosex² treatment—far farmer's practice; A mass trapping programme containing 20 standard yellow plastic funnel traps (Pheromone Chemicals Ltd.) per plot in 4 rows of 5 traps. The auto-confusion, FP-Near and Mass Trapping treatment plots were all 3 Ha in size and replicated three times whilst the FP-Far treatment was replicated four times to give a total of 13 plots. Three applications of the Exosex² YSB treatment were made on 20 January (16 days after transplanting (DAT)), 9 February (36 DAT) and 1 March (56 DAT) 2007. Individual units were attached to split bamboo canes (1.5 m long) by applying hand pressure to mould them onto the bamboo. The first application was placed approximately 0.7 m from the base of the canes and each subsequent application placed higher up the canes so that units were approximately at crop height throughout the trials. In farmer practice plots, pesticides were applied at the discretion of the farmers, 1 pesticide application was needed in the near FP treatment and 3 in the far FP treatment. Mass trapping was deployed 30 DAT and lures were subsequently changed at 46 and 61 DAT, 2 supplementary pesticide treatment were required.

| Results | | |
|---|---|---|
| Product and dosage | % deadheart damage at 55DAT | % white head damage at 88DAT |
| Exosex² 3.2 mg at 80 per ha | 1.56 | 2.82 |
| FP Near 1 treatment | 1.53 | 3.03 |
| FP Far 3 treatments | 1.22 | 3.25 |
| Mass Trapping 20 per ha + 2 pesticide | | 3.01 |

Based on the results from this trial it is concluded that the Exosex² auto-confusion system offers an efficacious, practical and cost effective alternative for control of *S. incertulas* in rice crops.

EXAMPLE 7

Exosex² SPL was formulated from 1% pheromone (Z9E12-14Ac), 0.5% flow agent, 19.5% paraffin wax and 79% carnauba wax. This powder was compacted into 1 g pellets.

In a commercial flour mill in Andover, UK the following 2 treatments were compared during the control of the Mediterranean flour moth, *Ephestia kuehniella*: Exosex² SPL at 4 units applied per 100 meters² with each compact containing 10 mg of active ingredient; Untreated control. Pheromone treatments were applied after a period of pretreatment monitoring and further Exosex² treatments were re-applied approximately 60 days after the first application and subsequent treatments. Exosex² units were applied without crushing the compacts directly into hanging devices that enable the male moths to contact the compact powder. These hanging devices containing the compacts were then placed directly on walls fittings, machinery, and guards. The Exosex² and control treatments both received cleaning treatments at regular scheduled timings. No other control measures have been used on either treatment.

| Results Mean Trap catches | | | |
|---|---|---|---|
| Treatment | Pre Treatment | 60 DAT | 136DAT |
| Exosex2 | 45.91 | 26.55 | 4.27 |
| Control | 26.33 | 26.0 | 54.0 |

DAT = Days after treatment

Based on the trap catches in this trial which are the usual indicator for additional control actions being required, the control population has progressively risen over the duration of the trial whilst the Exosex2 in its uncrushed state has successfully reduced the population to a barely detectable level in a food factory environment.

The invention claimed is:
1. A compact for insect control having a density of from 0.3 to 1 gcm$^{-3}$ consisting of
   particles of a first wax,
   particles of a second wax,
   and an active agent selected from the group consisting of an arthropod pesticide, an arthropod attractant, an arthropod semiochemical and a mixture of two or more of said group,
   the particles of said first wax and particles of said second wax having been compressed together for forming a friable solid,
   wherein said first wax is carnauba wax and said particles thereof are present in an amount of at least 51% by weight of said compact and said particles of said second wax are present in an amount of at least 19.5% by weight of said compact.

2. The compact of claim 1 wherein at least 80% by weight of said particles have a volume mean diameter of 50 microns or less.

3. The compact of claim 1 wherein at least some of said particles are at least partially coated by said active agent.

4. The compact of claim 1 wherein said second wax is selected from the group consisting of candelilla wax, microcrystalline wax, shellac wax, castor wax, ouricury wax and rice bran wax, paraffin wax, beeswax, lanolin, bayberry wax, sugar cane wax, ozocerite, ceresin wax, montan wax, and including mixtures of two or more thereof.

5. The compact of claim 1 wherein said second wax is comprised of paraffin wax.

6. The compact of claim 1 wherein said solid is in the form of a pellet.

7. A method of preparing the compact as defined in claim 1, said method comprising the steps of: providing the particles; exposing the particles to an active agent for associating said active agent with the particles; and compressing the particles associated with the active agent for forming said compact.

8. The compact of claim 4 wherein said solid is in the form of a pellet.

* * * * *